US00PP21866P3

(12) United States Plant Patent
Sonoda

(10) Patent No.: US PP21,866 P3
(45) Date of Patent: Apr. 12, 2011

(54) ***MANDEVILLA* LINDL PLANT NAMED 'TSURUMARUNOAKA5155'**

(50) Latin Name: *Mandevilla Sanderi*
Varietal Denomination: Tsurumarunoaka5155

(76) Inventor: Norio Sonoda, Kagoshima (JP)

( * ) Notice: Subject to any disclaimer, the term of this patent is extended or adjusted under 35 U.S.C. 154(b) by 0 days.

(21) Appl. No.: 12/458,645

(22) Filed: Jul. 17, 2009

(65) Prior Publication Data

US 2010/0031406 P1 Feb. 4, 2010

(30) Foreign Application Priority Data

Jul. 17, 2008 (JP) ..... 22767

(51) Int. Cl.
*A01H 5/00* (2006.01)

(52) U.S. Cl. ..... Plt./232

(58) Field of Classification Search ..... Plt./232
See application file for complete search history.

*Primary Examiner* — Susan B McCormick Ewoldt

(74) *Attorney, Agent, or Firm* — Westerman, Hattori, Daniels & Adrian, LLP

(57) ABSTRACT

A new and distinct *Mandevilla* plant named 'Tsurumarunoaka5155' of upright and vining plant habit, relatively small glossy foliage, freely branching habit, freely flowering habit, and being in full flower around Mother's Day as illustrated.

3 Drawing Sheets

*Mandevilla* LINDL plant named 'Tsurumarunouaka5155'
Latin name: *Mandevilla sanderi.*
Varietal denomination: 'Tsurumarunoaka5155'.

BACKGROUND OF THE INVENTION

In May, 2003, to obtain this variety, a red-based nameless variety of a culture line possessed by Applicant was crossbred with mixed pollens of nameless varieties of a culture line possessed by Applicant in a farm owned by Applicant in the town of Yusui-cho, Aira-gun, Kagoshima Pref., Japan. The red-based nameless variety grows slower and its flower is easy to be discolored by ultraviolet rays compared to 'Tsurumarunouaka5155'. Each of the nameless varieties grows a little faster and its flower is not easy to be discolored by ultraviolet rays compared to Tsuruhanbestpinki-1.

In February, 2004, after the above crossbreeding, a plant was grown and a resultant seed was planted into a soil on the farm to grow (germinate) and then bloom. This planting was carried out with the expectation that some varied plants could be obtained.

In April, 2005, from several hundreds of the flowering plants obtained by the above planting, one compact individual plant which grows faster and its flower is not easy to be discolored by ultraviolet rays appears. Then, to obtain a plant variety which grows faster and its flower is not easy to be discolored by ultraviolet rays, the above individual plant was selected and a branch (stem) thereof was removed and inserted in a soil to be grown (cutting, i.e., vegetative reproduction) and such a vegetative reproduction was repeated for propagation.

In June, 2006, the culture was completed after ensuring uniformity and stability. In other words, it was confirmed that the plant variety which grows faster and its flower is not easy to be discolored by ultraviolet rays can be obtained with uniformity and stability, the above repetition was completed.

SUMMARY OF THE INVENTION

1. Upright and vining plant habit.
2. Relatively small glossy foliage.

3. Freely branching habit.
4. Freely flowering habit.
5. Being in full flower around Mother's Day.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Mandevilla.*

DETAILED BOTANICAL DESCRIPTION

Figure 1:
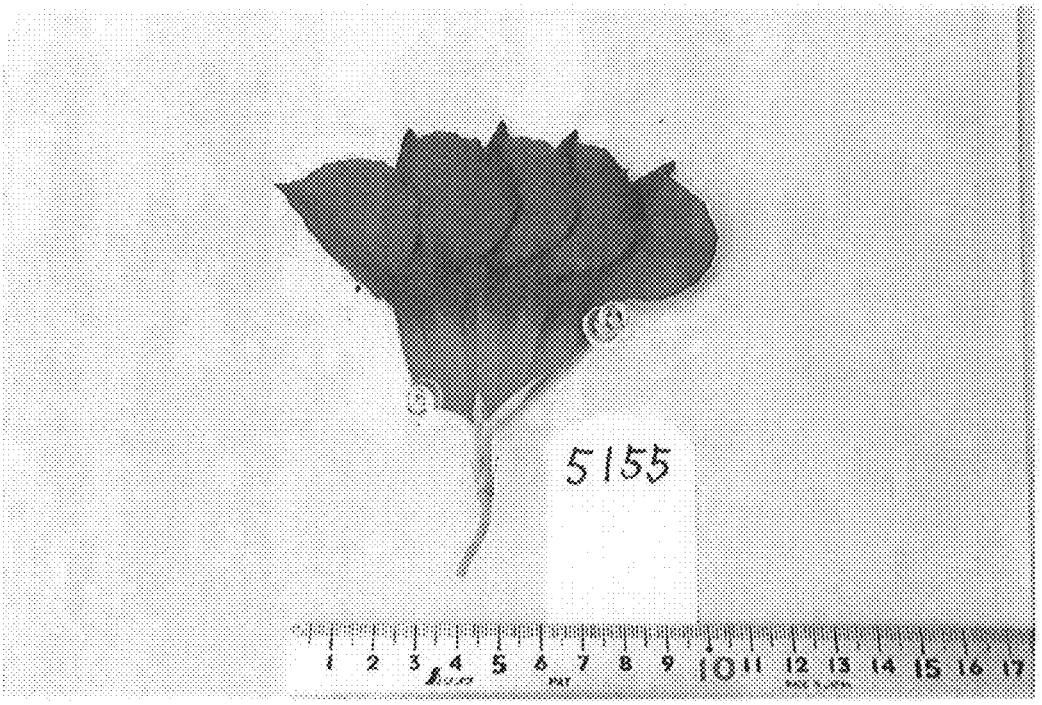
FIG. 1 is a diagrammatic view of the plant's flower, wherein the plant is 28 months old and some petals are removed so that a color of the inner side surrounded by petals and colors and shapes of the stamen and pistil can be seen.
Figure 2:
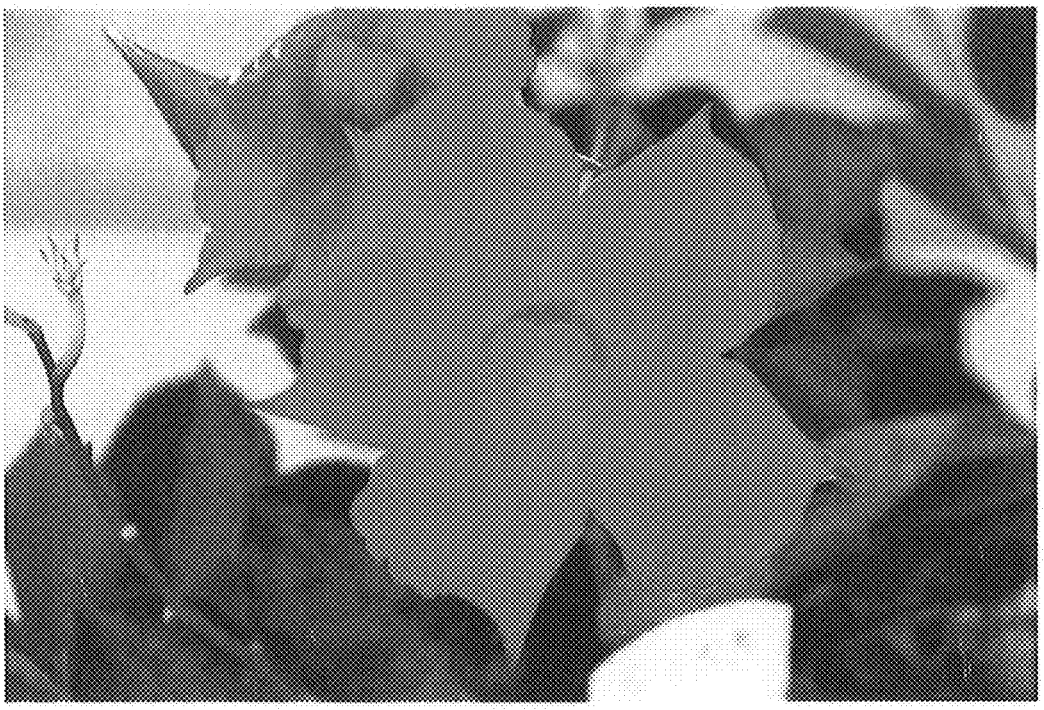
FIG. 2 is a close-up view of the plant's flower, wherein the plant is 28 months old.
Figure 3:
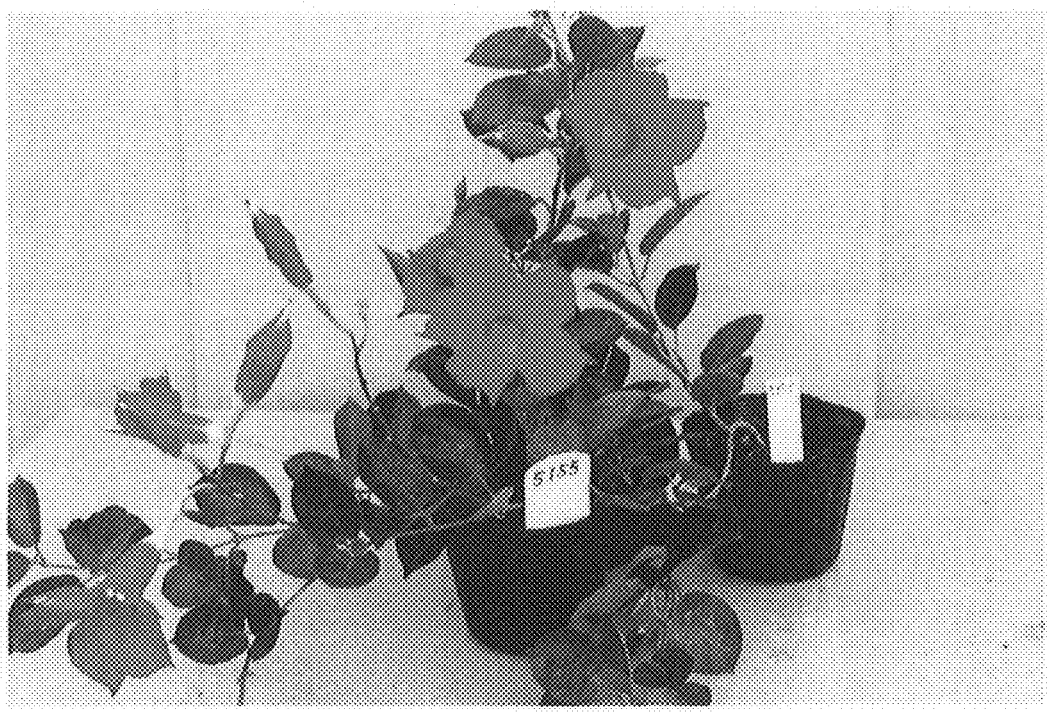
FIG. 3 is a full view of three plants, wherein the plants are 28 months old.
Figure 4:
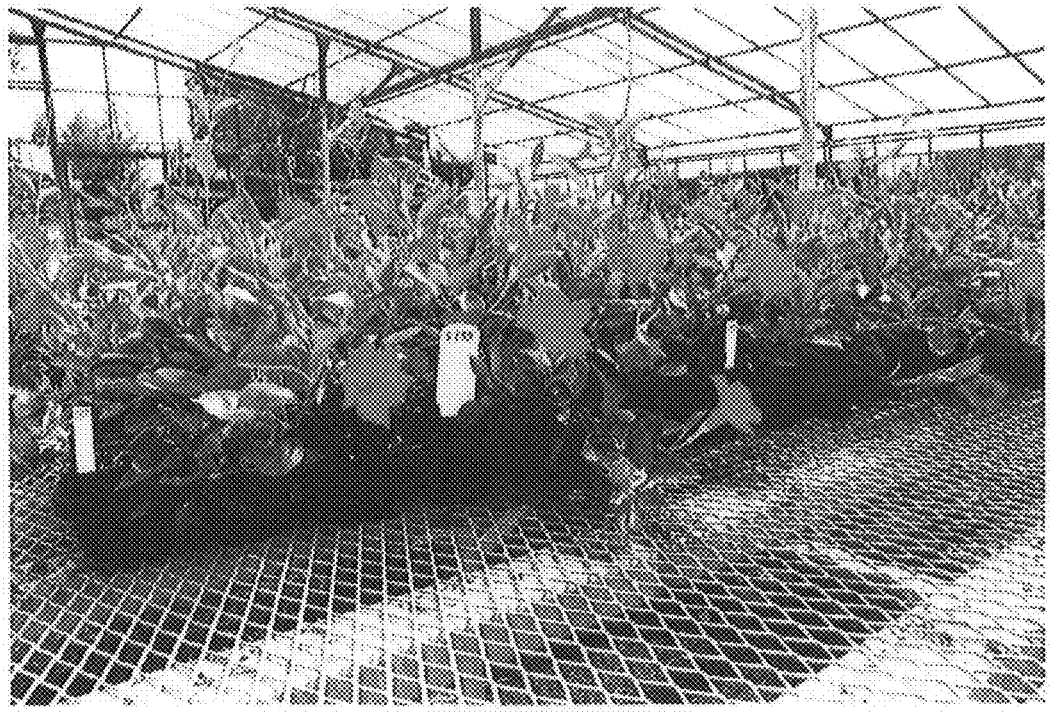
FIG. 4 is a close-up of the panoramic view of the cultivation area, wherein the plants are 28 months old.
Figure 5:
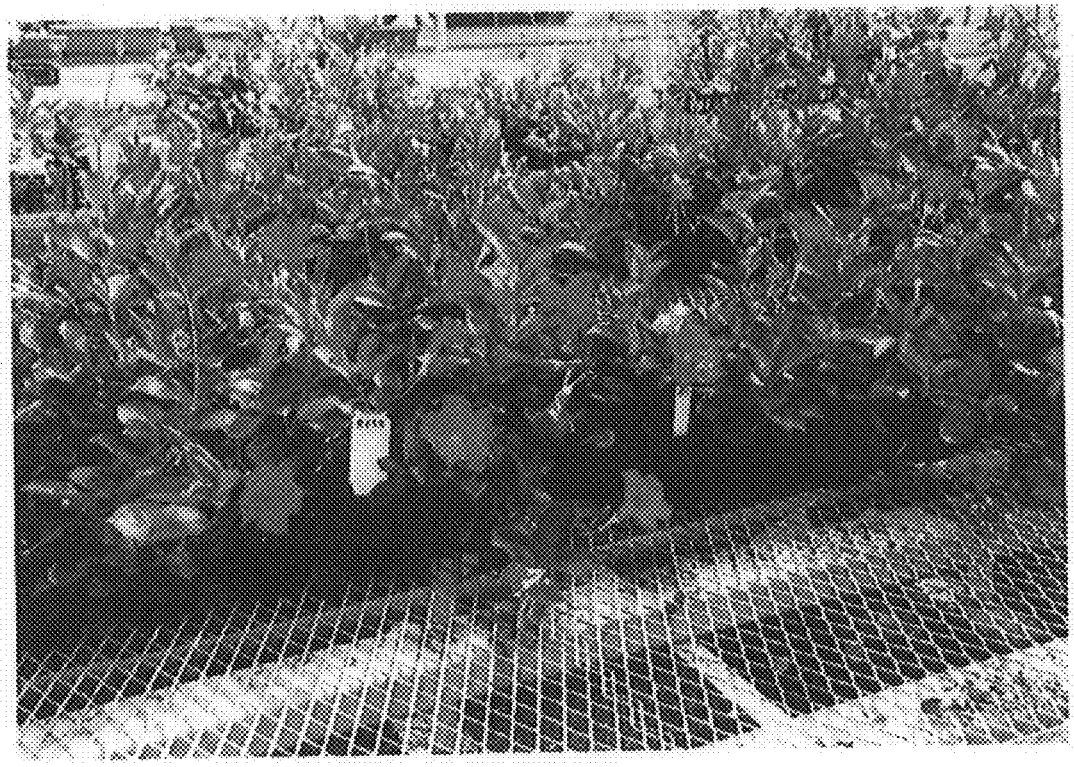
FIG. 5 is a panoramic view of the cultivation area, wherein the plants are 28 months old.

In the following description, color references are made to Japan Horticulture Standard Color Chart, edited as the 2nd print, resale on Sep. 10, 1997, except where general terms of ordinary dictionary significance are used. Plants used for the aforementioned photographs and following description were grown under conditions which closely approximate commercial production conditions during the early summer in a polyethylene covered greenhouse in the town of Yusui-cho, Aira-gun, Kagoshima Pref. in Japan. During the production of the plants, day temperatures averaged 26° C., and night temperatures averaged 14° C.

Propagation:

*Type.*—By vegetative cuttings.

*Time to initiate roots.*—About three weeks at 23° C. to 26° C.

*Time to produce a rooted young plant.*—About 40 days at 23° C. to 26° C.

*Root description.*—Fibrous, fleshy, white in color.

*Rooting habit.*—Freely branching.

Plant description:

*Form.*—Perennial — Upright and vining plant habit. Vigorous growth habit.

*Plant height.*—About 41 cm.

*Lateral branch description.*—Length: About 41 cm. Diameter: About 3 mm. Internode length: About 2.2 cm. Strength: Strong. Texture: Smooth, glabrous. Color, young: Close to Color Chart No. 3307. Mature: Close to Color Chart No. 1309.

Foliage description:

*Arrangement.*—Opposite, simple.

*Length.*—About 6.9 cm.

*Width.*—About 5 cm.

*Shape.*—Elliptic.

*Apex.*—Cuspidate.

*Base.*—Heart-shaped.

*Margin.*—Entire.

*Texture, upper and lower surfaces.*—Smooth, glabrous.

*Luster, upper and lower surfaces.*—Glossy.

*Venation pattern.*—Pinnate, reticulate.

*Color.*—Developing foliage, upper surface: Close to Color Chart No. 3508. Developing foliage, lower surface: Close to Color Chart No. 3506.

Fully expanded foliage, upper surface: Close to Color Chart No. 3716, Venation, Close to Color Chart No. 3712. Lower surface: Close to Color Chart No. 3508, Venation, Close to Color Chart No. 3508.

*Petiole length.*—About 1.6 cm.

*Petiole diameter.*—About 0.2 cm.

*Petiole texture, upper and lower surfaces.*—Sparsely pubescent.

*Petiole color, upper and lower surfaces.*—Close to Color Chart No. 3507.

Flower description:

*Flower type and habit.*—Single salverform flowers; flowers racemose; flowers face mostly outwardly, freely flowering habit, about five flowers per inflorescence.

*Natural flowering season.*—Long flowering period; Fully flowering from late spring to early summer in Japan; No flowering in midsummer, and then be in a flowering period again in late autumn.

*Flower longevity on the plant.*—About ten to fourteen days. Flowers not persistent.

*Fragrance.*—Not detected.

*Inflorescence length.*—6.5 cm.

*Inflorescence diameter.*—7.6 cm.

*Flowers.*—Appearance: Flared trumpet, corolla fused, five-parted; petals slightly imbricate; flowers roughly star-shaped. Diameter: 7.6 cm. Depth (length): 8.1 cm. Throat diameter: About 1.8 cm. Tube length: About 6.5 cm. Tube diameter, mid-section: 1.8 cm. Tube diameter, base: About 3 mm.

*Flower buds.*—Height: About 5.5 cm. Diameter: About 9 mm. Shape: Lenticular.

Color: Close to Color Chart No. 0409.

*Corolla.*—Arrangement/appearance: Single whorl of five petals, fused into flared trumpet; petals slightly imbricate. Petal length: About 3.2 cm. Petal width: About 3.5 cm. Petal shape: Spatulate. Petal apex: Acuminate. Petal margin: Entire, slightly wavy. Petal texture, upper and lower surfaces: Smooth, glabrous; velvety. Color: Petal, when opening and fully opened, upper surface: Close to Color Chart No. 0409; Lower surface: Close to Color Chart No. 0408.

*Sepals.*—Arrangement/appearance: Five per flower in a single whorl; fused.

Length: About 10 mm. Width: About 4 mm. Shape: Lanceolate. Apex: Acute. Margin: Entire. Texture, upper and lower surfaces: Smooth, glabrous. Color, immature, upper and lower surfaces: Close to Color Chart No. 3704; towards the apex, close to Color Chart No. 0405. Color, mature, upper and lower surfaces: Close to Color Chart No. 3704; towards the apex, close to Color Chart No. 0405.

*Peduncles.*—Length: About 8.0 cm. Diameter: About 3.5 mm. Texture: Smooth, glabrous. Strength: Flexible, but strong. Color: Close to Color Chart No. 3507.

*Pedicels.*—Length: About 2.2 cm. Diameter: 3 mm. Texture: Smooth, glabrous, flexible, but strong. Color: Close to Color Chart No. 3507.

*Reproductive organs.*—Stamens: Quantity/arrangement: Typically five; filament fused to corolla; anthers, connivent. Anther shape: Elliptic. Anther size: About 8 mm by 1 mm. Anther color: Close to Color Chart No. 2505. Pollen amount: Scarce. Pollen color: Close to Color Chart No. 2506. Pistils: Quantity: Typically one. Pistil length: About 2.2 cm. Stigma shape: Conical. Stigma color: Close to Color Chart No. 3506. Ovary color: Close to Color Chart No. 3506.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 5° C. to about 37° C.

The flower of the 'Hannyajisenred6106' (U.S. Plant application Ser. No. 12/588,097) is smaller than that of the 'Tsurumarunouaka5155' as a whole and bright in color, and the peripheral of the petal of the 'Hannyajisenred6106' is not undulated.

The flower of the 'Kedoaka5152' (U.S. Plant application Ser. No. 12/588,099) is remarkably brighter in color than that of the the 'Tsurumarunouaka5155'.

The flower of the 'Sawaranoured5134' (U.S. Plant application Ser. No. 12/588,100) is deep red and dark in color and easy to be discolored by ultraviolet rays compared to the 'Tsurumarunouaka5155'.

What is claimed is:

1. A new and distinct *Mandevilla* plant named 'Tsurumarunoaka5155' as illustrated and described.

* * * * *